(12) United States Patent
Steele et al.

(10) Patent No.: US 11,103,654 B2
(45) Date of Patent: Aug. 31, 2021

(54) TAMPER-EVIDENT CLOSURE (71) Applicant: NORDSON CORPORATION, Westlake, OH (US)

(72) Inventors: Kyle R. Steele, Windsor, CO (US); Peter D. Lewis, Loveland, CO (US); Douglas Kimmel, Nunn, CO (US)

(73) Assignee: Nordson Corporation, Westlake, OH (US)

( * ) Notice: Subject to any disclaimer, the term of this patent is extended or adjusted under 35 U.S.C. 154(b) by 216 days.

(21) Appl. No.: 15/892,181

(22) Filed: Feb. 8, 2018

(65) Prior Publication Data

US 2019/0240425 A1    Aug. 8, 2019

(51) Int. Cl.
| | |
|---|---|
| *A61M 5/50* | (2006.01) |
| *A61M 5/32* | (2006.01) |
| *A61J 1/14* | (2006.01) |
| *B65D 41/34* | (2006.01) |
| *A61M 5/31* | (2006.01) |

(52) U.S. Cl.
CPC .......... *A61M 5/5086* (2013.01); *A61J 1/1418* (2015.05); *A61M 5/3134* (2013.01); *A61M 5/3202* (2013.01); *B65D 41/3428* (2013.01)

(58) Field of Classification Search
CPC .... A61M 5/5086; A61M 5/50; A61M 5/3202; A61M 2005/3104; A61J 1/14; A61J 1/1418; A61J 1/1425; A61J 1/1412
See application file for complete search history.

(56) References Cited

U.S. PATENT DOCUMENTS

| | | | |
|---|---|---|---|
| 3,630,403 A | 12/1971 | Berg | |
| 4,433,789 A | 2/1984 | Gibilisco | |
| 4,723,673 A | 2/1988 | Tartaglia et al. | |
| 4,740,205 A * | 4/1988 | Seltzer | A61B 5/150587 604/192 |
| 4,844,273 A | 7/1989 | Hawkins | |
| 5,328,474 A | 7/1994 | Raines | |

(Continued)

FOREIGN PATENT DOCUMENTS

| | | |
|---|---|---|
| WO | WO2010091522 A2 | 8/2010 |
| WO | WO2018024624 A1 | 2/2018 |

OTHER PUBLICATIONS

ISA/220—Notification of Transmittal of Search Report and Written Opinion of the ISA, or the Declaration dated Jun. 5, 2019 for WO Application No. PCT/US19/013743.

(Continued)

*Primary Examiner* — Nilay J Shah
(74) *Attorney, Agent, or Firm* — BakerHostetler (57) ABSTRACT

A tamper-evident closure assembly includes a connector, a tamper element removably affixed to the connector, and a cap having an interior surface defining a receptacle, where a portion of the connector is within the receptacle and the cap is configured to engage with the tamper element. The tamper element is configured to be separated from the connector upon application of a removal force and to be retained within the receptacle of the cap so that it can later be removed from the receptacle. A kit for a tamper-evident closure assembly includes a cap having an interior surface defining a receptacle, a tamper element configured to engage with the cap within the receptacle, and a housing configured to receive the cap.

25 Claims, 9 Drawing Sheets

(56) References Cited

U.S. PATENT DOCUMENTS

| | | | |
|---|---|---|---|
| 5,624,402 A | 4/1997 | Imbert | |
| 5,688,241 A * | 11/1997 | Asbaghi | A61M 5/326 604/110 |
| 5,716,678 A | 2/1998 | Rockrath et al. | |
| 5,749,484 A | 5/1998 | Trout | |
| 5,779,075 A | 7/1998 | Salmon et al. | |
| 5,807,345 A | 9/1998 | Grabenkort | |
| 6,027,482 A | 2/2000 | Imbert | |
| 6,068,614 A | 5/2000 | Kimber et al. | |
| 6,190,364 B1 | 2/2001 | Imbert | |
| 6,196,998 B1 | 3/2001 | Jansen et al. | |
| 6,491,665 B1 | 12/2002 | Vetter et al. | |
| 6,520,935 B1 | 2/2003 | Jansen et al. | |
| 6,585,691 B1 | 7/2003 | Vitello | |
| 6,773,415 B2 | 8/2004 | Heiniger | |
| 6,821,268 B2 | 11/2004 | Balestracci | |
| 6,921,383 B2 | 7/2005 | Vitello | |
| 7,374,555 B2 | 5/2008 | Heinz et al. | |
| 7,425,208 B1 | 9/2008 | Vitello | |
| 7,632,244 B2 | 12/2009 | Buehler et al. | |
| 7,762,988 B1 | 7/2010 | Vitello | |
| 7,882,977 B2 | 2/2011 | Johnson | |
| RE42,355 E | 5/2011 | Heiniger | |
| 8,118,788 B2 | 2/2012 | Frezza | |
| 8,231,025 B2 | 7/2012 | Johnson | |
| 8,348,895 B1 | 1/2013 | Vitello | |
| 8,353,869 B2 * | 1/2013 | Ranalletta | A61M 5/50 604/111 |
| 8,443,999 B1 | 5/2013 | Reinders | |
| 8,591,462 B1 | 11/2013 | Vitello | |
| RE44,640 E | 12/2013 | Heiniger | |
| 8,616,413 B2 | 12/2013 | Koyama | |
| 8,784,377 B2 | 7/2014 | Ranalletta et al. | |
| 8,864,021 B1 * | 10/2014 | Vitello | A61M 5/5086 235/375 |
| 8,864,707 B1 | 10/2014 | Vitello | |
| 8,864,708 B1 | 10/2014 | Vitello | |
| 8,882,719 B2 | 11/2014 | Manke et al. | |
| 8,950,939 B2 | 2/2015 | Last et al. | |
| 9,095,667 B2 | 8/2015 | Von Schuckmann | |
| 9,199,749 B1 | 12/2015 | Vitello et al. | |
| 9,309,032 B2 | 4/2016 | Berge et al. | |
| 9,311,592 B1 | 4/2016 | Vitello et al. | |
| 9,402,967 B1 | 8/2016 | Vitello | |
| 9,463,310 B1 | 10/2016 | Vitello | |
| 9,533,802 B2 | 1/2017 | Berge | |
| 9,545,484 B2 | 1/2017 | Bicknell et al. | |
| 9,617,045 B2 | 4/2017 | Reinders | |
| 9,821,152 B1 | 11/2017 | Vitello et al. | |
| 9,861,767 B2 | 1/2018 | Okihara et al. | |
| 9,919,113 B2 | 3/2018 | Mermet | |
| 9,937,301 B2 | 4/2018 | Ward | |
| 9,938,050 B2 | 4/2018 | Berge | |
| 9,981,785 B2 | 5/2018 | Berge | |
| 2008/0097310 A1 * | 4/2008 | Buehler | A61M 5/50 604/111 |
| 2015/0165122 A1 | 6/2015 | Pommereau et al. | |
| 2015/0246185 A1 | 9/2015 | Heinz | |
| 2016/0022925 A1 | 1/2016 | Zenker | |
| 2016/0176550 A1 | 6/2016 | Viitello et al. | |
| 2018/0099097 A1 | 4/2018 | Pommereau et al. | |

OTHER PUBLICATIONS

ISA/206—Invitation to Pay Additional Fees dated Apr. 5, 2019 for WO Application No. PCT/US19/013743.

* cited by examiner

TAMPER-EVIDENT CLOSURE

TECHNICAL FIELD

The present disclosure generally relates to tamper detection devices, and, more particularly, to tamper-evident closure assemblies for medical devices.

BACKGROUND

Many industrial applications require mechanisms that prevent tampering with a particular product. This is especially the case in the medical profession, where it is important for medical staff and patients to be aware of any tampering to a medical device or substance. Existing technology for detecting and preventing tampering is often cumbersome, difficult to use, increases risks of injury to the user, and increases the chance of contamination of the patient or of the medical environment. Therefore, there is a need for improved systems and devices for detecting tampering with a device in a safe and efficient manner.

SUMMARY

Devices and methods for tamper-evident closure assemblies are disclosed. In one embodiment, a tamper-evident closure assembly for use with a medical device includes a connector having a proximal end that defines a connection interface thereon, a tamper element removably affixed to the connector, and a cap having an interior surface defining a receptacle such that a portion of the connector is within the receptacle. The cap is configured to engage with the tamper element, and the tamper element is configured to be separated from the connector upon application of a removal force. Upon application of the removal force, the tamper element is separated from the connector and is retained within the receptacle of the cap. The connector is then removable from the receptacle.

In another embodiment, a kit for a tamper-evident closure assembly includes a cap having an interior surface defining a receptacle, a tamper element configured to engage with the cap within the receptacle, and a housing configured to receive the cap. The cap is removably secured to the housing.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings.

DETAILED DESCRIPTION OF ILLUSTRATIVE EMBODIMENTS

Systems and methods are disclosed for providing tamper-evident closure assemblies for medical devices. The tamper-evident assembly includes a connector with which the assembly connects to a medical device and a tamper-evidence mechanism that informs the user of tampering. Once tampering has been identified, the user may take appropriate steps to remedy the problem.

In some exemplary embodiments, the tamper-evident assemblies are disclosed for use with medical devices, but it will be understood that such assemblies can be used in other, non-medical environments. Referring to FIGS. 1-6, a tamper-evident assembly 100 is depicted and includes a connector 110 and a cap 150. The connector 110 has a distal end 111 and proximal end 112 opposite the distal end 111. The proximal end 112 defines a connection interface 113 that removably connects to an external tool, for example a medical device. In some embodiments, the connector 110 may be substantially cylindrical, but it will be understood that the specific shape of the connector 110 is not limited by this disclosure.

Figure 1:
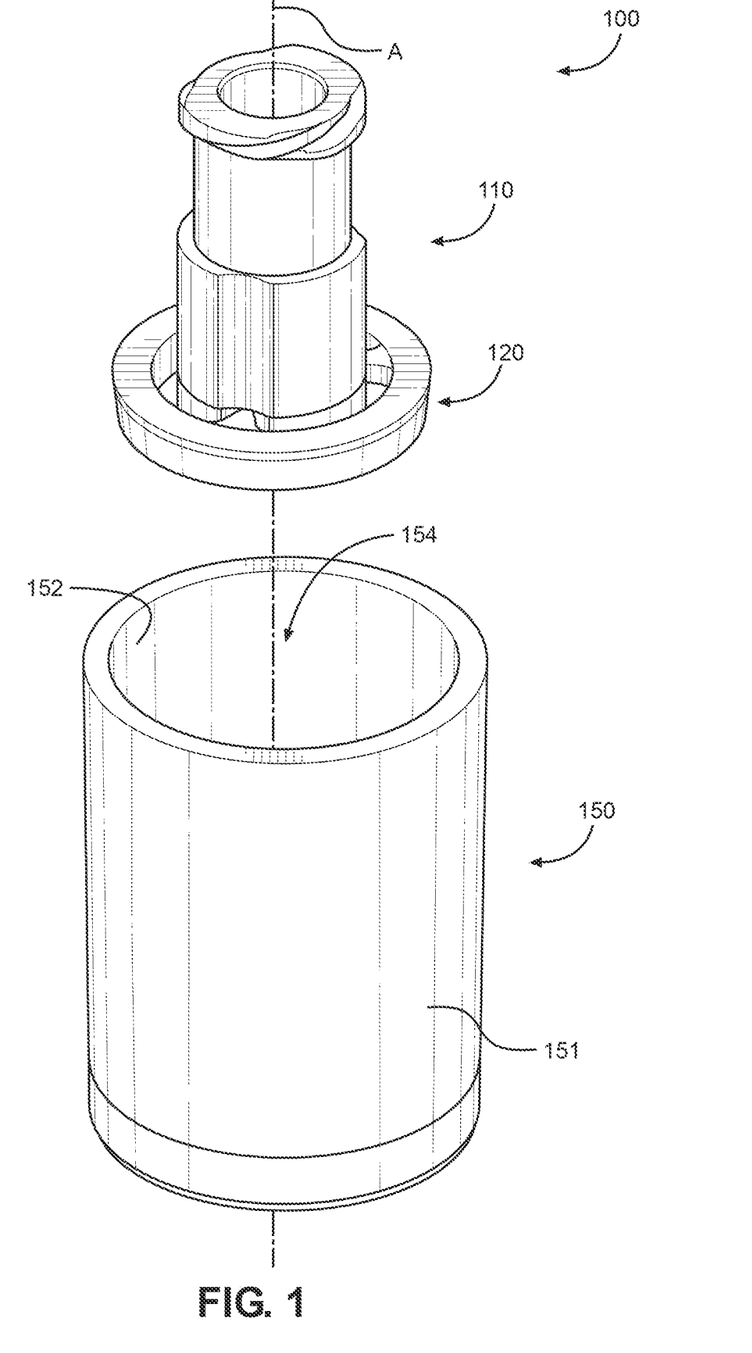
FIG. 1 illustrates an exploded isometric view of a tamper-evident closure assembly according to an embodiment.
Figure 2:
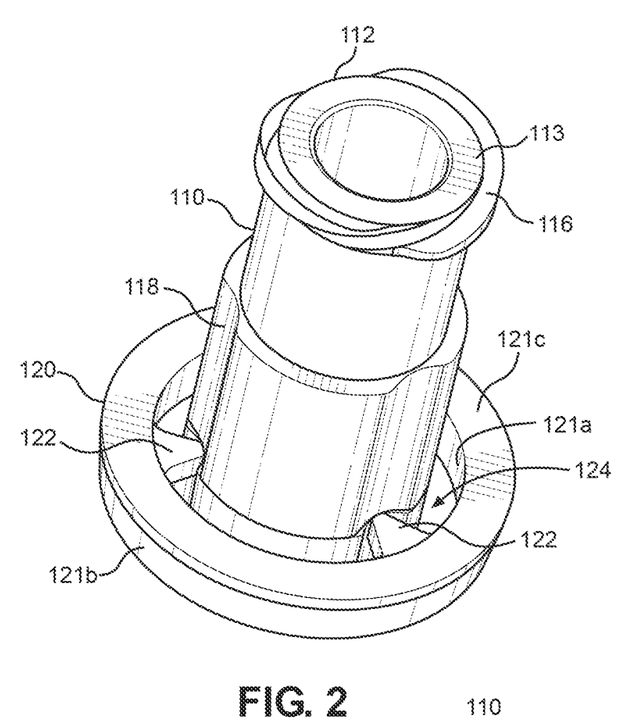
FIG. 2 illustrates an isometric view of a connector and tamper element according to an embodiment.
Figure 3:
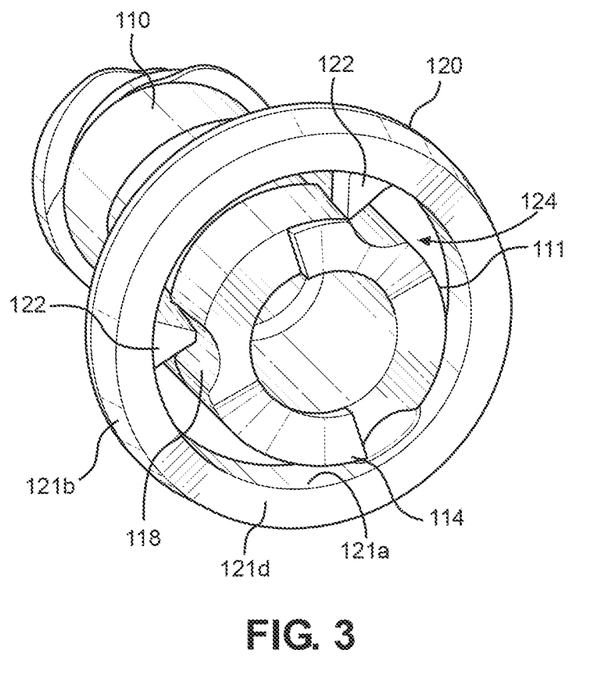
FIG. 3 illustrates an isometric view from another angle of the connector and tamper element of FIG. 2.

A tamper element 120 is affixed to the connector 110. The tamper element 120 serves to indicate that the cap 150 has been removed from the connector 110, and that the connector 110 may have been accessed. The tamper element 120 is removably attached to the body of the connector 110 and may comprise an integral piece with the connector 110. Referring to FIGS. 1-3, the tamper element 120 may have a substantially round shape and may be formed as a ring having an interior surface 121a defining an inner diameter and an exterior surface 121b defining an outer diameter.

The tamper element 120 may be attached to the connector 110 via one or more protrusions 122 extending from the tamper element 120 to the body of the connector 110. The protrusions 122 define a gap 124 in the space between the connector 110 and the tamper element 120. Referring to the exemplary embodiment of FIGS. 1-3, three protrusions 122 may extend from the interior surface 121a of the ring-shaped tamper element 120 to the connector 110. In some embodiments, the protrusions 122 may extend from a different portion of the tamper element 120, for example, from the exterior surface 121b of the ring, from a top surface 121c, and/or from a bottom surface 121d. Although FIGS. 1-3 depict an embodiment having three protrusions 122, it will be understood that the tamper element 120 may include a different number of protrusions, for example, 1, 2, . . . , 8, or another suitable number of protrusions 122.

In some embodiments, the connector 110 includes one or more scallops or grooves 118 configured to receive the one or more protrusions 122. The grooves 118 preclude any sharp edges from broken pieces of the connector or tamper element to extend beyond the outer diameter of the connector 110. This increases safety and improves handling and disposing the device.

In alternative embodiments, the tamper element 120 may be affixed to the connector 110 without protrusions 122 or a gap 124.

The connector 110 with the attached tamper element 120 may be inserted into the cap 150 along an insertion axis A. Referring to FIGS. 1-6, the cap 150 includes an exterior surface 151 and an interior surface 152 that defines a receptacle 154. The receptacle 154 is configured to receive the connector 110 and the tamper element 120. In some embodiments, the entirety of the tamper element 120 and at least a portion of the connector 110 are within the receptacle 154. The cap 150 is configured to receive and retain the tamper element 120 such that, once inserted, the tamper element 120 cannot be removed from the receptacle 154.

The receptacle 154 includes an unlocked portion 154*a* and a locked portion 154*b*. The tamper element 120 may freely move within the unlocked portion 154*a*. Once the tamper element 120 passes into the locked portion 154*b*, the tamper element 120 is retained within the locked portion 154*b* such that it cannot be removed.

Figure 4:
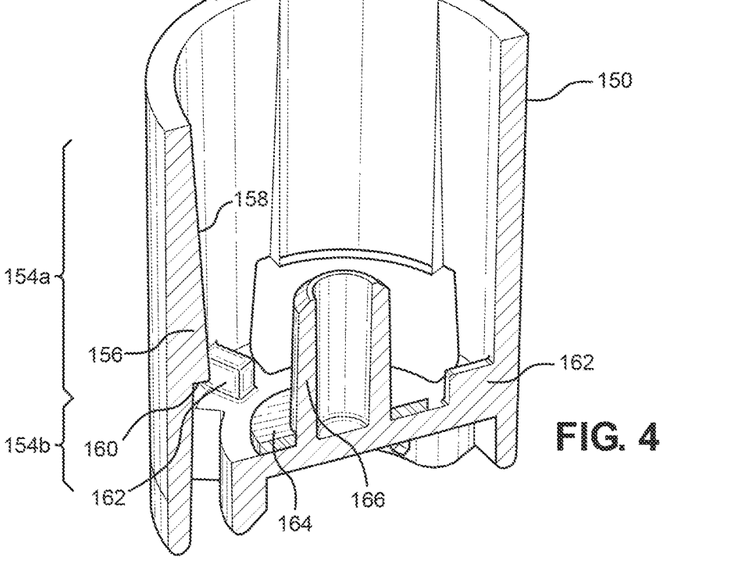
FIG. 4 illustrates a cross-sectional view of a cap according to an embodiment.
Figure 5:
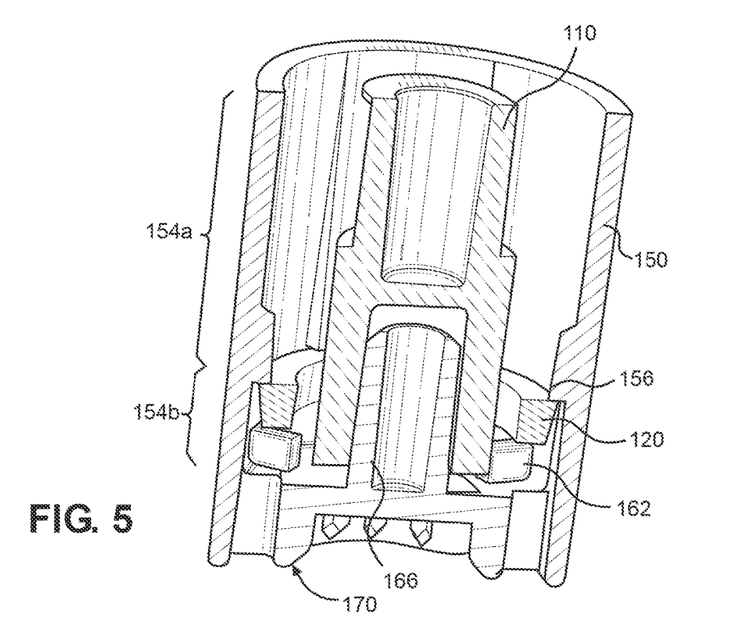
FIG. 5 illustrates a cross-sectional view of the tamper-evident closure assembly of FIG. 1.
Figure 6:
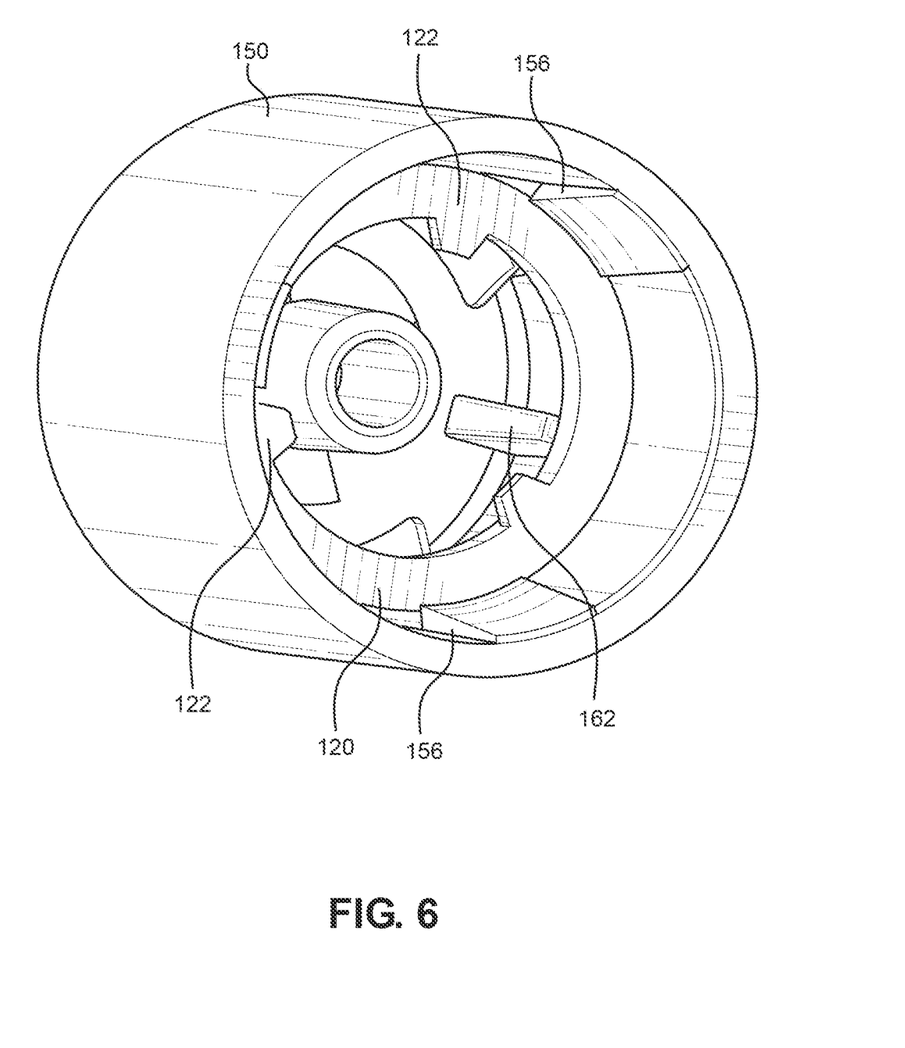
FIG. 6 illustrates an isometric view of a cap with a tamper element according to an embodiment.

Referring to FIGS. 4-6, the cap 150 may include one or more retention members 156 to engage the tamper element 120. The retention members 156 may define the transition between the unlocked portion 154*a* and the locked portion 154*b*. Each retention member 156 may include a sloped surface 158 disposed within the unlocked portion 154*a* and a retention surface 160 in the locked portion 154*b*. It will be understood that the cap 150 is not limited to having a particular number of retention members and may include, for example, 1, 2, . . . , 8, or another quantity of retention members 156.

The tamper element 120 may slidably contact the sloped surface 158 when inserted into the receptacle 154. In some embodiments, the exterior surface 121*b* of the tamper element 120 may be tapered to correspond to the sloped surface 158 to facilitate insertion into the cap 150. As the tamper element 120 moves into the locked portion 154*b*, the retention surface 160 may contact the top surface 121*c* of the tamper element 120 such that the tamper element 120 cannot move back into the unlocked portion 154*a*. In such embodiments, the tamper element 120 may be configured such that once it moves in a first insertion direction where that the top surface 121*c* passes over the retention surface 160, the tamper element 120 can no longer be moved in the opposite direction out of the locked portion 154*b*.

To access the connector 110 when the connector 110 and the tamper element 120 are within the receptacle 154, the connector 110 may be forcefully separated from the tamper element 120 and removed from within the cap 150. Once separated, the connector 110 and tamper element 120 are not configured to be reattached. In some embodiments, the connector 110 may lack a means of being retained within the cap 150 when it is separated from the tamper element 120.

When separated from the tamper element 120, the connector 110 is removable from the cap 150 and can be accessed by a user. The connector 110 can be removed by hand or engaged with an external tool, another connector, or a medical device. The connector 110 separate from the tamper element 120 indicates that the connector 110 may have been removed from the cap, accessed, or tampered with.

The tamper element 120 is configured to be removed from the connector 110 upon application of sufficient force. When the tamper element 120 is retained within the locked portion 154*b*, the cap 150 and the connector 110 cannot be easily separated. If a sufficient removal force is applied to either the cap 150 or the connector 110 to withdraw the connector 110 from within the receptacle 154, the tamper element 120 may separate from the connector 110 and remain within the cap 150. The connector 110 is then separated and removable from the cap 150.

In embodiments having one or more protrusions 122, each protrusion 122 may break so as to separate the tamper element 120 from the connector 110. Alternatively, if the tamper element 120 is affixed to the connector 110 directly without protrusions 122, the tamper element 120 may break off from the connector 110 at the connection interface upon application of the removal force.

While this disclosure is not limited to any particular amount of removal force, it will be understood that disengaging the tamper element 120 from the connector 110 can be done without external tools and by an average user. Suitable force, for example, may include between about 1 and about 5 lbf, between about 2 and about 4 pound-force, between about 2.5 and about 3 lbf, or combinations of the above. In some embodiments, for example, an average user may be able to exert enough force with a single hand. Force may be applied along the insertion axis A of the connector 110 and tamper element 120 into the cap 150. In some embodiments, force may also be applied rotationally around the insertion axis A or at an angle to the insertion axis A. The removal force may be applied to the connector 110, the tamper element 120, and/or the cap 150. In some embodiments, force may be applied to an external tool fixedly connected to one or more of the above components.

Referring again to FIGS. 4-6, in some embodiments, the cap 150 may include one or more projections 162 within the receptacle 154. When the tamper element 120 is within the locked portion 154*b*, the projections 162 may engage the bottom surface 121*d* of the tamper element 120 to maintain the tamper element 120 in substantially the same horizontal plane defined by the top or bottom surfaces 121*c*, 121*d*. The projections 162 prevent the tamper element 120 from twisting and falling out of the cap 150 when the tamper element 120 is separated from the connector 110. In some embodiments, the cap 150 may include one projection 162 that extends around the perimeter of the interior surface 152. Alternatively, the cap 150 may include 2, 3, . . . , 8, or another suitable number of projections 162.

The distance between the projection 162 and the retention surface 160 may be equal to or greater than the thickness of the tamper element 120, measured, for example, from the top surface 121*c* to the bottom surface 121*d*. In some embodiments, the distance between the retention surface 160 and the projection 162 may be greater than the thickness of the tamper element 120 to provide tolerance for the tamper element 120 to enter the locked portion 154*b*. The greater space allows for the tamper element 120 to move into the locked portion 154*b* without unnecessary friction or resistance, which could otherwise contribute to inadvertent or premature separation of the tamper element 120 from the connector 110.

In some embodiments, the cap 150 may have no projections 162, and the tamper element 120 may be retained between the retention surface 160 and the interior surface 152 without use of a projection 162.

In some embodiments, the cap 150 may further include a post 166 disposed within the receptacle 154. Referring to the exemplary embodiments of FIGS. 4-6, the post 166 may be substantially cylindrical and attached to the interior surface 152 of the cap 150. The post 166 is configured to engage with the connector 110 when the connector 110 is inserted into the receptacle 154. In some embodiments, the post 166 may contact the distal end 111 of the connector 110. The post 166 may keep the connector 110 aligned with the insertion axis A when the connector 110 is within the cap 150 such that the connector 110 does not slide, rotate, or translate in an undesired manner. This may improve rigidity of the assembly and decrease instances of inadvertent disengagement, crimping of components, or damage to one or more components in the assembly or attached thereto.

The tamper element 120 separated from the connector 110 may be readily detected by a user. In some embodiments, the tamper element 120 may be visible and visually discernable from the interior of the cap 150 from at least one viewing angle. Referring to the exemplary embodiment of FIG. 6, the tamper element 120 may be visible by looking into the receptacle 154 from the opening through which the connector 110 was inserted and removed. In another embodiment, one or more additional openings (not shown) may be present on the cap 150 such that the tamper element 120 is visible through the one or more additional openings.

In another embodiment, the tamper element 120 may be physically discernable by touch. One or more portions of the tamper element 120 may be configured to extend through and beyond the surface of the cap 150, such that a user may tactilely feel the extension when the tamper element 120 is within the receptacle 154. In some embodiments, one or more portions of the tamper element 120 may have a surface with a texture that is different from that of the cap 150 such that a user can feel the different texture of the tamper element 120 when it is held in the receptacle 154.

In some embodiments, the tamper-evident assembly 100 may include an indicator (not shown) that provides a signal to a user that the tamper element 120 is retained within the cap 150. The indicator may be a physical indicator, for example, a switch configured to be in a first position when the tamper element 120 is not in the receptacle 154 and in a second position when the tamper element 120 is in the receptacle 154.

It will be understood that this disclosure does not limit the specific dimensions of the connector 110, cap 150, tamper element 120, or other components of the tamper-evident assembly 100. In some embodiments, the tamper element 120 may be within the locked portion 154b when the tamper element 120 is substantially centered in the cap 150 along the insertion axis A. In alternative embodiments, the cap 150, the tamper element 120, and the connector 110 may be designed and manufactured such that the locked portion 154b is disposed closer to one end of the cap 150 than to another end, such that the tamper element 120 can be engaged closer to one end than another. Such embodiments may improve stability of the interacting components and decrease the risk of inadvertent disengagement or damage to one or more components of the tamper-evident assembly.

In another embodiment, the locked portion 154b may be disposed near the center of the cap 150 along the insertion axis A such that the tamper element 120 is engaged at the approximate center of the cap 150. It will be understood that various components described throughout this application may also be designed and manufactured to have corresponding shapes and dimensions to provide suitable functionality in the various embodiments above. For example, the post 166 may be designed to be shorter or longer depending on whether the locked portion 154b is closer to one end of the cap 150 or to another end.

Figure 7:
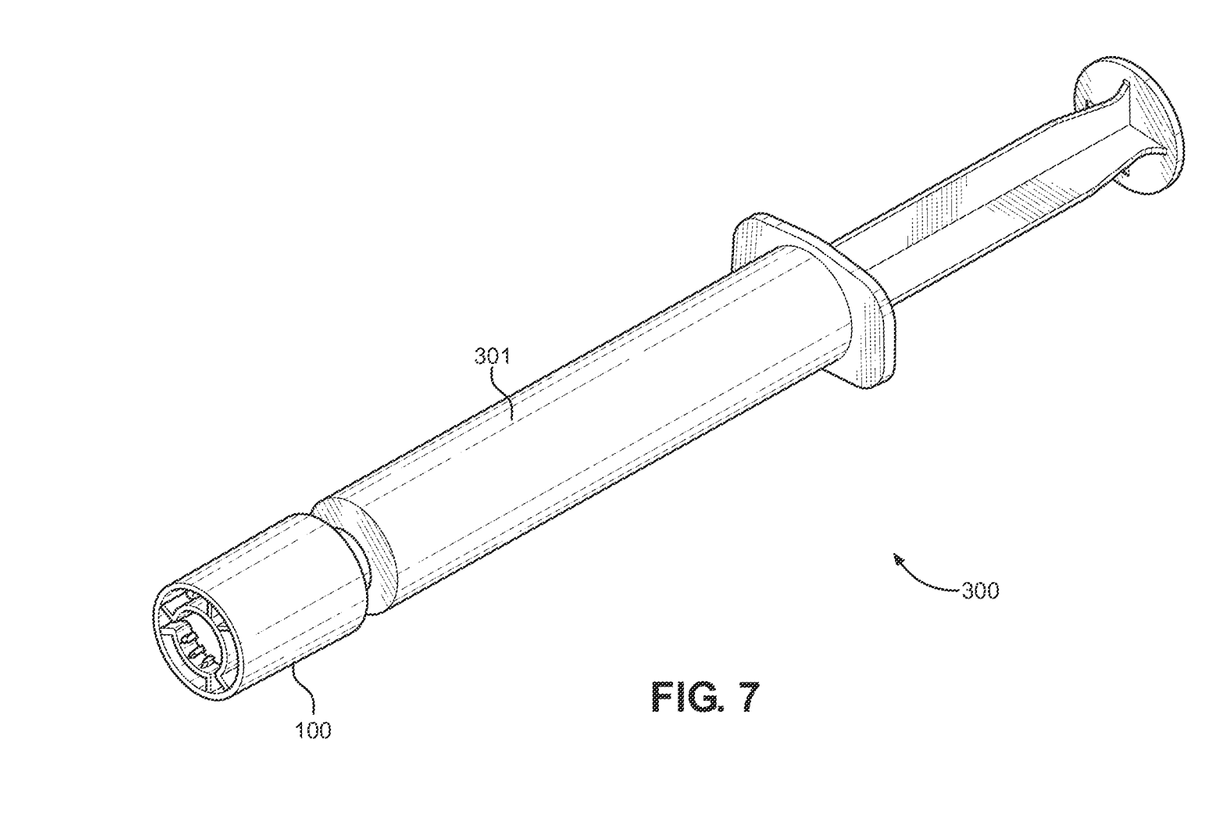
FIG. 7 illustrates an isometric view of a system with a tamper-evident closure assembly according to an embodiment.

The tamper-evident assembly 100 may be used with various devices, for example medical devices. Suitable medical devices may include, but are not limited to, syringes, bottles, tubes, or other medical devices that may benefit from a closure assembly that indicates prior tampering, or attempted tampering, with the assembly or the medical device. Referring to the illustrative embodiment of a system 300 in FIG. 7, the tamper-evident assembly 100 may be fixedly attached to a syringe 301.

The tamper-evident assembly 100 may be manufactured, sold, and distributed as a stand-alone component that can be adapted to a desired use or device. Alternatively, the tamper-evident assembly 100 may be manufactured, sold, and distributed affixed to a desired device and intended for a specific use. Referring again to FIG. 7, the system 300 may be sold as an individual unit including the tamper-evident assembly 100 fixedly attached to the syringe 301. The syringe 301 may be prefilled with a desired medicinal substance before distribution. Distributing a prefilled syringe 301 with an attached tamper-evident assembly 100 can help the end user discern between a syringe 301 that has not been tampered with and one that may have been tampered with or otherwise accessed in the time between being filled and reaching the user.

It will be understood that the tamper-evident assembly 100 may be attached to a desired device in a variety of ways, and that this disclosure is not limited to a particular method of connecting the tamper-evident assembly 100 to a device. Referring once more to FIGS. 1-6, the connector 110 may include a connection interface 113 at the proximal end 112. The connection interface 113 may attach to an external device or tool via a known connection method, such as via snap fitting, friction fitting, threading, or another suitable connection method. Referring to the exemplary embodiment of FIGS. 2 and 3, the connection interface 113 may include threads 116 configured to engage with corresponding threads (not shown) on an external tool.

In some embodiments, when the connector 110 is attached to the tamper element 120 and is within the receptacle 154, the connection interface 113 is also within the receptacle 154. This placement may be advantageous because the connection interface 113 cannot be readily accessed without at least partially removing the connector 110 from the cap 150, thus separating the connector 110 from the tamper element 120. This may be advantageous by ensuring that the connected device, for example a prefilled syringe, has not been accessed after being connected to the tamper-evident assembly 100.

The tamper-evident assembly 100 may be manufactured and distributed with the connector 110 and tamper element 120 being separate from the cap 150. In such embodiments, a user may attach the connector 110 to an external tool or device, for example a syringe, and then insert the connector 110 with the tamper element 120 into the cap. Alternatively, the user may engage the tamper element 120 on the connector 110 with the cap 150 prior to affixing the assembly to the external device or tool.

In another embodiment, the tamper-evident assembly 100 may be manufactured and distributed with the connector 110 and tamper element 120 already inserted into and engaged with the cap 150. The user may affix the assembly 100 with the external device or tool.

Referring again to FIGS. 4-6, the cap 150 may be designed to communicate with the connector 110 in such a manner that the cap 150 and the connector 110 are rotated to engage the tamper-evident assembly 100 with the external device or tool. As shown in FIGS. 4-6, the cap may include a first ratcheting ramp 164 defined by the interior surface 152. It will be understood that any suitable number of first ratcheting ramps 164 could be present, for example, 1, 2, 3, 4, or another acceptable number.

The connector 110 may include a second ratcheting ramp 114 that is configured to engage with the first ratcheting ramp 164. The connector 110 may include 1, 2, 3, 4, or any other suitable number of second ratcheting ramps 114. In some embodiments, the number of first ratcheting ramps 164 is equal to the number of second ratcheting ramps 114.

To engage the tamper-evident assembly 100 with an external device, an attachment force may be applied to one or more components of the assembly or to the external device. In some embodiments where the connector 110 is configured to threadably engage with a corresponding threaded interface (not shown) of the external device, one or more components of the tamper-evident assembly 100 may be rotated to actuate said engagement. In such embodiments, when the cap 150 is rotated in a first direction (e.g., clockwise around the insertion axis A), the first ratcheting ramp 164 disposed on the cap 150 also moves and forcibly contacts the second ratcheting ramp 114. As force is exerted on the second ratcheting ramp 114 that is fixedly disposed on the connector 110, the connector 110 also rotates in the same first direction (e.g., clockwise around the insertion axis A), and the connection interface 113 engages with the external device. When the cap 150 is rotated in a second direction opposite the first direction (e.g., counterclockwise around the insertion axis A), the first ratcheting ramp 164 slidably contacts the second ratcheting ramp 114 and slides along it, such that even when the cap 150 continues to rotate in the second direction, the rotational force transferred to the second ratcheting ramp 114 is insufficient to rotate the connector 110. This decreases the possibility of disengaging the tamper-evident assembly 100 from the external device after it has been engaged.

In some embodiments, the cap 150 may have a first position relative to the connector 110 and a second position that is axially displaced from the first position along the insertion axis A. In the first position, the first ratcheting ramp 164 is at least partially located in the same plane as the second ratcheting ramp 114 such that the two ramps can contact each other upon rotation of the cap 150. In the second position, the cap 150 is axially displaced a sufficient distance such that the plane in which the first ratcheting ramp 164 lies does not overlap the plane in which the second ratcheting ramp 114 lies. When the cap 150 is in the second position, neither rotation in the first direction nor rotation in the second direction results in contact between the first and second ratcheting ramps 164, 1.

Figure 8:
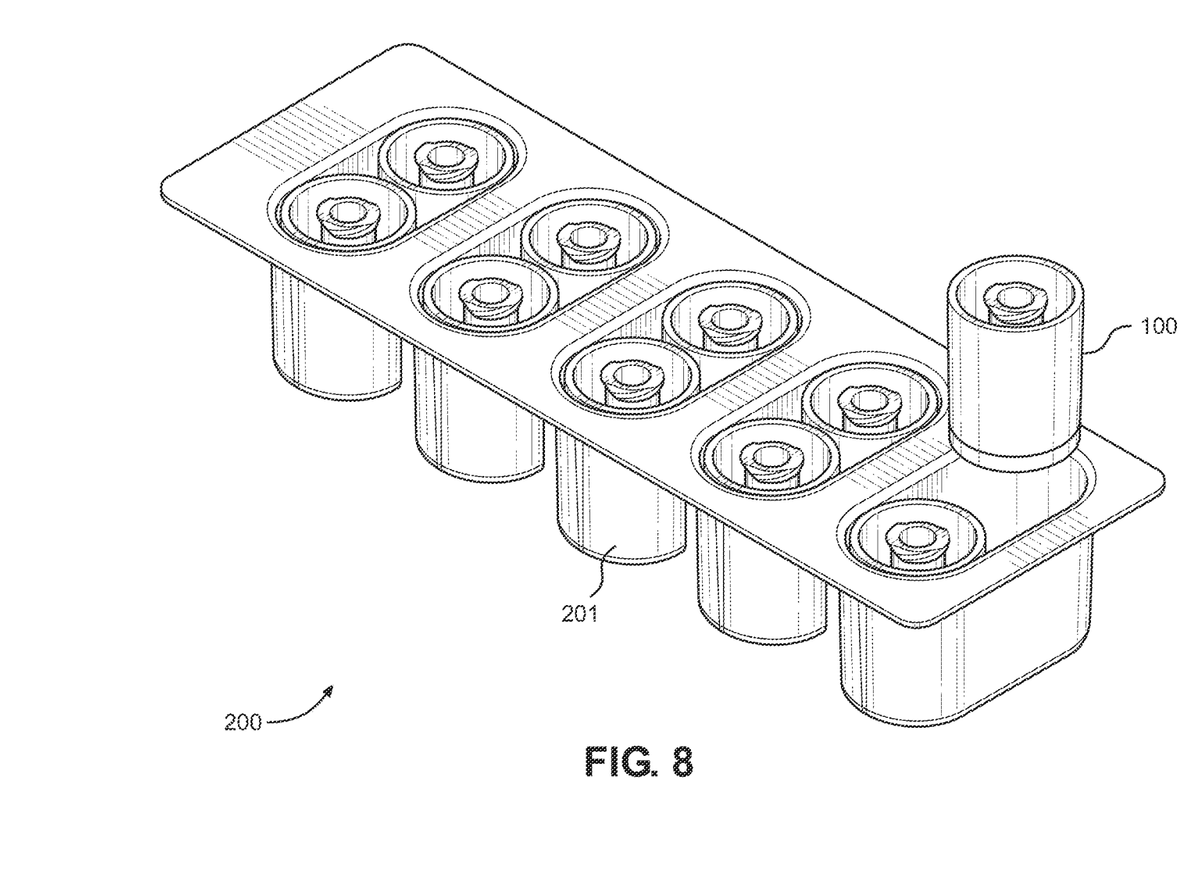
FIG. 8 illustrates an isometric view of a kit with a tamper-evident closure assembly according to an embodiment.
Figure 9:
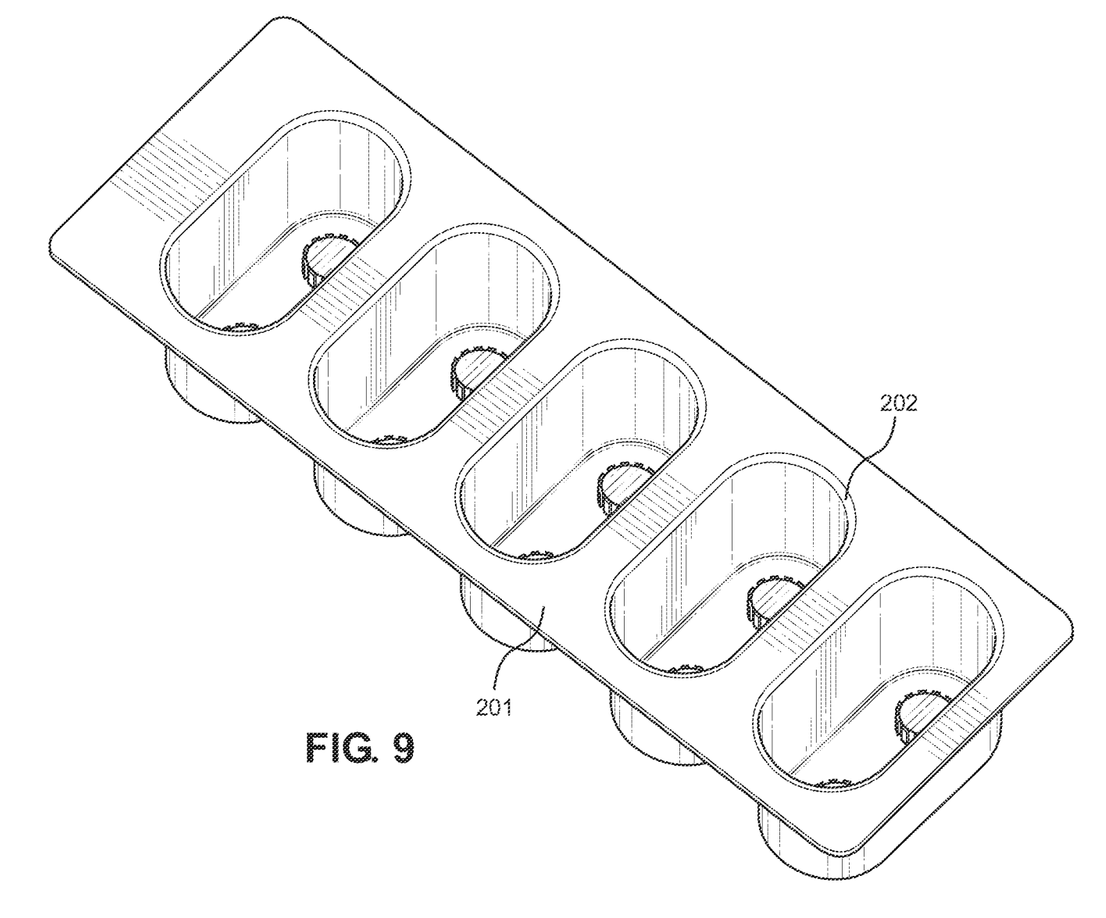
FIG. 9 illustrates an isometric view of a housing according to an embodiment.

The tamper-evident assembly may be manufactured and distributed individually or as part of a set of multiple assemblies. Referring to FIGS. 8-11, a kit 200 includes a housing 201 containing a plurality of tamper-evident assemblies 100 that are removable for use. Although FIG. 8 depicts a kit 200 having one housing 201 that contains ten tamper-evident assemblies 100, it will be understood that kits having other quantities and arrangements of housings and assemblies are covered by this disclosure. In some embodiments, for example, the kit 200 may include 1, 2, 3, 4, or another number of housings 201.

Each housing 201 may contain 1, 2, . . . , 20, or another suitable number of tamper-evident assemblies 100. The housing 201 may include the same assemblies, or it may contain a variety of assembly embodiments as disclosed throughout this specification. As depicted in the illustrative embodiment of FIG. 8, the housing 201 may have five compartments 202, each configured to receive two tamper-evident assemblies 100. It will be understood that this disclosure is not limiting to any particular arrangement of the housing 201 or the compartment 202. In some embodiments, a housing 201 may include 1, 2, . . . , 10, or another suitable number of compartments 202. Each compartment 202 may be configured to receive and removably contain 1, 2, . . . , 6, or another suitable number of tamper-evident assemblies 100.

Figure 10:
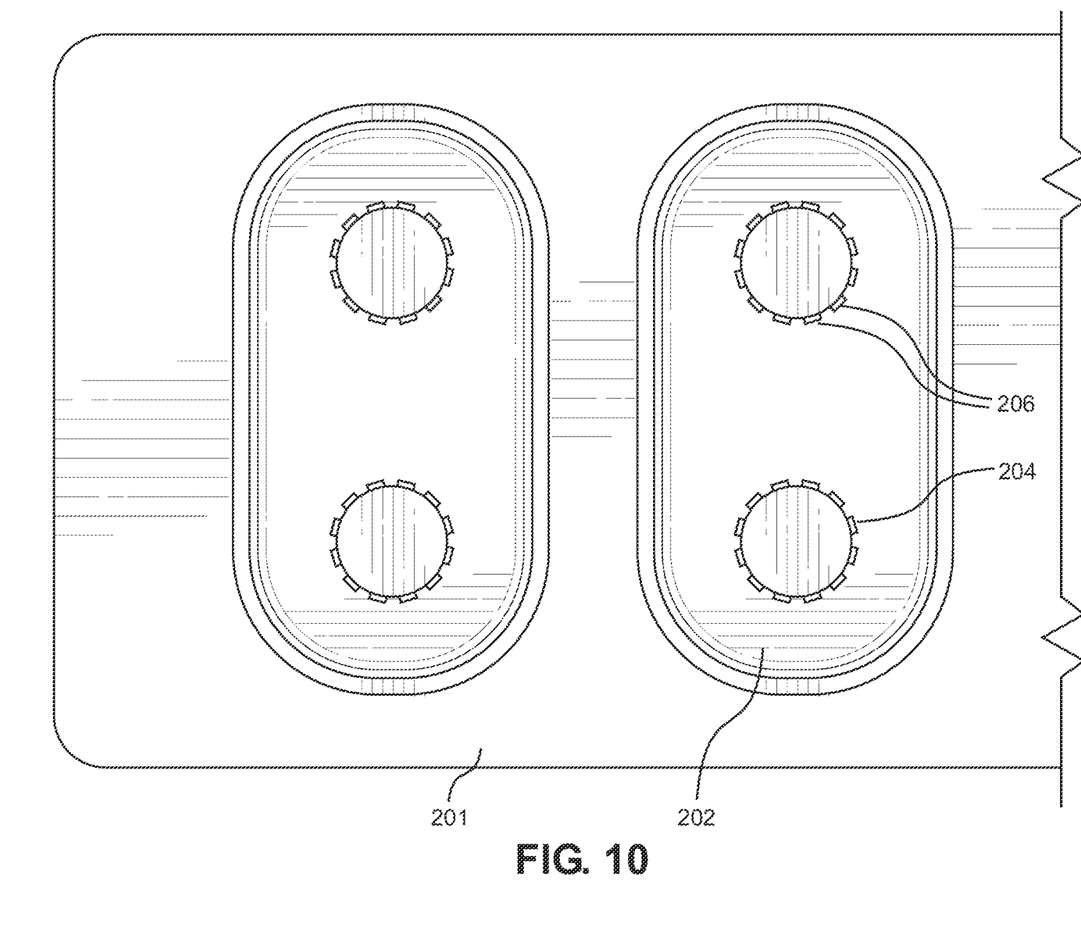
FIG. 10 illustrates; a top perspective view of a portion of the housing of FIG. 9.
Figure 11:
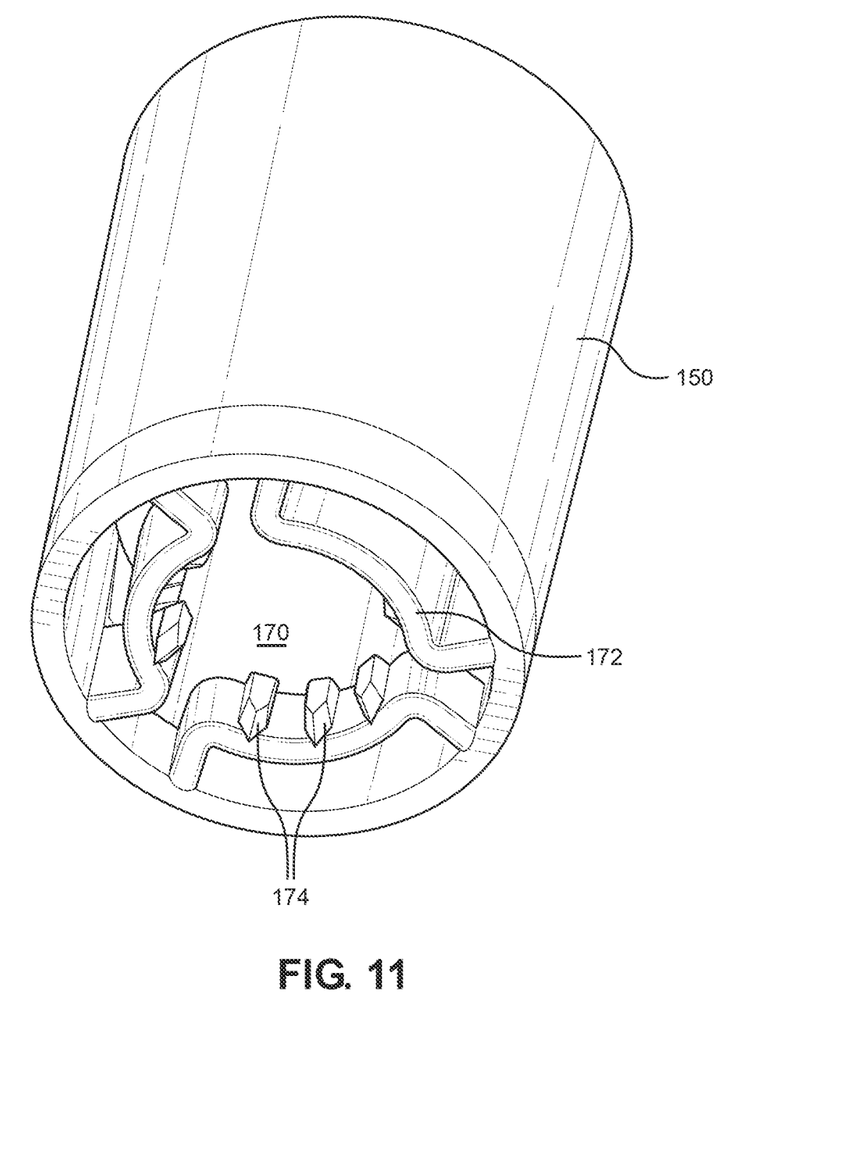
FIG. 11 illustrates an isometric view of a cap according to an embodiment.

Referring to FIGS. 10 and 11, the tamper-evident assembly 100 may include a fitment 170 configured to engage with the housing 201. The housing 201 may include a corresponding fixture 204 configured to receive the fitment 170 and removably retain the tamper-evident assembly 100 on or within the housing 201. The tamper-evident assembly 100 may be affixed to the housing 201 by any acceptable means, for example, via snap fitting, friction fitting, threading, or another suitable connection method.

Referring to the exemplary embodiment of FIG. 11, the fitment 170 may include one or more walls 172. The walls 172 provide increased contact area with the corresponding fixture 204. Although FIG. 11 is depicted having three walls 172, this disclosure is not limited to a particular number of walls, and a suitable fitment 170 may include 0, 1, 2, 3, 4, 5, 6, or another acceptable number of walls 172.

In some embodiments, a plurality of teeth 174 may be disposed on the fitment 170, on the walls 172, or on both the fitment and the walls. The teeth 174 project in a direction away from the wall 172 or from the fitment 170, and are configured to increase retention of the tamper-evident assembly 100 in the housing 201. In some embodiments, the fixture 204 may include a plurality of teeth 206 configured to interact and engage with the teeth 174 on the fitment 170. It will be understood that the quantity of teeth depicted in the illustrative embodiments is not limiting, and other acceptable quantities of teeth 174, 206 are covered by this disclosure.

Providing a kit 200 with multiple tamper-evident assemblies 100 allows for a user to quickly and easily attach an assembly to an external device. The housing 201 presents a larger component for better gripping and handling, which lowers the possibility of mishandling or dropping the assembly during attachment of an external device. The housing 201 additionally allows a user to avoid handling the assembly itself, thus improving cleanliness, maintaining sterility, and decreasing the chance of contamination.

A kit 200 having a plurality of assemblies 100 improves efficiency, as a user does not need to acquire individual packages of assemblies. In some embodiments, the kit 200 may include a specific quantity and assortment of tamper-evident assemblies 100 that may be necessary for a particular procedure. In such a case, a user has to acquire, prepare, open, and utilize only the relevant desired kit or kits 200 rather than individually searching for and preparing an assortment of various assemblies.

In some embodiments, it may be desirable for a tamper-evident assembly 100 to be connected with an external device by use of separate machinery (not shown). Examples of machinery may include user-operated apparatuses as well as robotic devices having automated processes. In such embodiments, the kit 200 may be configured to be loaded into the machinery such that each tamper-evident assembly 100 can then be connected to the desired external device. In some embodiments, multiple assemblies may be connected to multiple external devices simultaneously to increase throughput and save time.

The kit 200 improves longevity and decreases costs associated with distributing the tamper-evident assemblies 100. The housing 201 offers added protection to the assemblies therein, which reduces instances of damage to the components during packaging, shipping, distribution, storage, and preparation. In some embodiments, the added protection by the housing 201 may allow for thinner and cheaper materials to be used in manufacturing of the tamper-evident assemblies 100 that would otherwise be unsuitable due to greater expected physical stresses on the products.

The components described throughout this specification can be manufactured using various materials, for example metals, plastics, rubbers, or a combination of metal, plastic, and rubber. In some embodiments, multiple materials may be used for various components. In some embodiments, it may be advantageous to use materials that can be subject to sterilization for use in a medical environment. It will be understood that this disclosure is not limited to particular materials used, and that other combinations of suitable materials may be used.

The embodiments disclosed herein offer a number of advantages. The tamper-evident assembly 100 allows a user to quickly and accurately detect any tampering of the assembly or the device to which it is connected. In the medical field, this decreases the risk of inadvertently administering an incorrect medicinal substance to a patient. Furthermore, once the tamper element 120 is disposed in the locked portion 154b, in some embodiments it cannot be moved back to the unlocked portion 154a. To disengage the assembly from the external device, the tamper element 120 is separated from the connector 110 and remains within the cap 150. This serves to alert another user at a later time that the device where the tamper element 120 is within the cap 150 and is separated from the connector 110 has already been used, opened, accessed, or otherwise tampered with. Such indication to the user helps decrease risk of infection from reusing certain medical devices, for example, syringes, or distributing contaminated or incorrect medical products.

The tamper-evident assembly 100 allows a user to easily and quickly discern whether the assembly has been tampered with. This saves time by allowing the user to quickly identify a tampered-with product and dispose of it accordingly. Such embodiments additionally lower uncertainty about the safety of each assembly by informing the users of the tamper status quickly. This helps reduce stress that users may experience when working with potentially-accessed or tampered-with products in a fast-paced environment.

The present disclosure offers various advantages over existing anti-tamper technology. Many current options require removal of a portion of the device to indicate tampering. For example, some existing assemblies require breaching or breaking a ring or a protrusion surrounding the assembly. This approach results in extraneous pieces of the assembly that need to be removed. In a medical scenario, loose pieces may not be desirable because they may cause contamination of tools and/or infection in the patient. Additionally, breaking or removing a portion of the assembly exposes sharp edges, the locations and angles of which are often difficult to predict. This may result in direct injury to the user and/or the patient, or in indirect risk of contamination or infection due to ripped gloves or the loose edges catching on tools or materials The disclosed embodiments offer ergonomic handling of the product to assist with proper use. The ergonomic assemblies do not require excessive strength for proper use, making them available to a wider range of professionals. Existing technology often requires direct access to the connecting interfaces of the devices, which may expose users to greater risk of injury, for example, contacting sharp edges, needles, or dangerous substances within the device.

While systems and methods have been described in connection with the various embodiments of the various figures, it will be appreciated by those skilled in the art that changes could be made to the embodiments without departing from the broad inventive concept thereof. It is understood, therefore, that this disclosure is not limited to the particular embodiments disclosed, and it is intended to cover modifications within the spirit and scope of the present disclosure as defined by the claims.

Certain terminology is used in the description for convenience only and is not limiting. The words "proximal" and "distal" generally refer to positions or directions toward and away from, respectively, an individual using the mixing system. The words "axial", "vertical", "transverse", "left", "right", "above," and "below" designate directions in the drawings to which reference is made. The term "substantially" is intended to mean considerable in extent or largely but not necessarily wholly that which is specified. The terminology includes the above-listed words, derivatives thereof and words of similar import.

The term "plurality," as used herein, means more than one. The singular forms "a," "an," and "the" include the plural reference, and reference to a particular numerical value includes at least that particular value, unless the context clearly indicates otherwise.

What is claimed:

1. A tamper-evident closure assembly for use with a medical device, the assembly comprising:
   a connector having a proximal end that defines a connection interface;
   a tamper element removably affixed to the connector such that the tamper element forms one integral piece with the connector, the tamper element configured to be separated from the connector upon application of a removal force; and
   a cap having an interior surface defining a receptacle, the cap being configured to engage with the tamper element, such that at least a portion of the connector is within the receptacle,
   wherein upon application of the removal force, the tamper element is separated from the connector and retained within the receptacle of the cap, and the connector being removable from the receptacle,
   wherein the interior surface of the cap defines a retention member configured to prevent the tamper element from being removed from the receptacle, the retention member having a distally facing retaining surface, the interior surface of the cap and the retaining surface of the retention member defining a locking portion of the receptacle,
   wherein a proximal end of the tamper element defines a proximally facing surface that is configured to abut the retaining surface to prevent the tamper element from moving past the retention member out of the locking portion, and
   wherein the entire tamper element is distally spaced from the connection interface of the connector.

2. The assembly of claim 1, wherein the tamper element is affixed to the connector via a protrusion extending from the tamper element to the connector, such that a gap is defined between the tamper element and the connector.

3. The assembly of claim 1, wherein the retention member has a sloped surface and the retaining surface is adjacent the sloped surface,
   wherein the sloped surface is configured to allow the tamper element to slidably move past the retention member into the locking portion.

4. The assembly of claim 3, wherein the tamper element in the locking portion is disposed closer to one end of the cap than to another end of the cap.

5. The assembly of claim 3, wherein the interior surface of the cap further defines a projection configured to contact the tamper element when the tamper element is within the locking portion of the receptacle.

6. The assembly of claim 1, wherein when the tamper element is separated from the connector and retained within the cap, the tamper element is visible inside the receptacle from at least one angle.

7. The assembly of claim 1, wherein the connection interface includes a Luer connector.

8. The assembly of claim 1, wherein the interior surface of the cap further defines a post configured to contact the connector when the connector and the tamper element are retained in the receptacle of the cap, the post being configured to decrease movement of the connector within the cap after being inserted into the receptacle.

9. The assembly of claim 1, wherein the cap further defines a fitment configured to engage with a housing.

10. The assembly of claim 1, wherein the tamper element is a ring.

11. The assembly of claim 1, wherein the entire proximally facing surface is flat, and the tamper element has an axial length less than an axial length of the connector.

12. A tamper-evident closure assembly for use with a medical device, the assembly comprising:
   a connector having a proximal end that defines a connection interface;
   a tamper element removably affixed to the connector such that the tamper element forms one integral piece with the connector, the tamper element configured to be separated from the connector upon application of a removal force; and
   a cap having an interior surface defining a receptacle, the cap being configured to engage with the tamper element, such that at least a portion of the connector is within the receptacle,
   wherein upon application of the removal force, the tamper element is separated from the connector and retained within the receptacle of the cap, and the connector being removable from the receptacle,
   wherein the tamper element is affixed to the connector via a protrusion extending from the tamper element to the connector, such that a gap is defined between the tamper element and the connector, and
   wherein the connector further defines a groove configured to receive the protrusion extending from the tamper element to the connector when the protrusion is affixed to the connector.

13. The assembly of claim 12, wherein the protrusion is affixed to a radially outwardly facing surface, of the connector, that defines the groove.

14. A tamper-evident closure assembly for use with a medical device, the assembly comprising:
   a connector having a proximal end that defines a connection interface;
   a tamper element removably affixed to the connector such that the tamper element forms one integral piece with the connector, the tamper element configured to be separated from the connector upon application of a removal force; and
   a cap having an interior surface defining a receptacle, the cap being configured to engage with the tamper element, such that at least a portion of the connector is within the receptacle,
   wherein upon application of the removal force, the tamper element is separated from the connector and retained within the receptacle of the cap, and the connector being removable from the receptacle,
   wherein the cap further includes a first ratcheting ramp configured to contact a corresponding second ratcheting ramp on the connector,
   wherein when the connector is rotated in a screwing direction, the first ratcheting ramp contacts the second ratcheting ramp on the connector, such that the cap is also rotated in the screwing direction,
   and when the connector is rotated in an unscrewing direction opposite the screwing direction, the first ratcheting ramp slidably contacts the second ratcheting ramp on the connector, such that the first ratcheting ramp slides along the second ratcheting ramp and the cap is not rotated in the unscrewing direction.

15. The assembly of claim 14, wherein the first ratcheting ramp defines a sloped proximally facing surface that is configured to contact a sloped distally facing surface defined by the corresponding second ratcheting ramp.

16. A kit for a tamper-evident closure assembly, the kit comprising:
   a connector having a proximal end that defines a connection interface;
   a cap having an interior surface defining a receptacle;
   a tamper element affixed to the connector such that the tamper element forms one integral piece with the connector, the tamper element configured to engage with the cap within the receptacle; and
   a housing configured to receive the cap, the cap being removably secured to the housing,
   wherein the interior surface of the cap defines a retention member configured to prevent the tamper element from being removed from the receptacle, the retention member having a distally facing retaining surface, the interior surface of the cap and the distally facing retaining surface of the retention member defining a locking portion of the receptacle,
   wherein a proximal end of the tamper element defines a proximally facing surface that is configured to abut the distally facing retaining surface to prevent the tamper element from moving past the retention member out of the locking portion, and
   wherein the entire tamper element is distally spaced from the connection interface of the connector.

17. The kit of claim 16, further comprising a plurality of caps, and where the housing is configured to receive any one of the plurality of caps.

18. The kit of claim 16, wherein the tamper element is configured to attach to a medical device.

19. The kit of claim 16, wherein the tamper element is affixed to the connector, the connector being configured to attach to a medical device.

20. The kit of claim 19, wherein the tamper element is configured to separate from the connector when a removal force is applied to the tamper element or to the connector.

21. The kit of claim 20, wherein the tamper element is configured to remain within the receptacle when the tamper element is separated from the connector.

22. The kit of claim 16, wherein the cap defines a fitment and the housing defines a fixture, wherein the fitment is configured to engage with the fixture, such that the cap is retained in the housing.

23. The kit of claim 22, wherein the fitment includes a plurality of teeth and the fixture includes a plurality of teeth, wherein the plurality of teeth on the fitment of the cap are configured to releasably engage with the plurality of teeth on the fixture of the housing.

24. A tamper-evident closure assembly for use with a medical device, the assembly comprising:
- a connector having a proximal end that defines a connection interface;
- a tamper element removably affixed to the connector such that the tamper element forms one integral piece with the connector, the tamper element configured to be separated from the connector upon application of a removal force; and
- a cap having an interior surface defining a receptacle, the cap being configured to engage with the tamper element, such that at least a portion of the connector is within the receptacle,
- wherein upon application of the removal force, the tamper element is separated from the connector and retained within the receptacle of the cap, and the connector being removable from the receptacle,
- wherein the interior surface of the cap defines a retention member configured to prevent the tamper element from being removed from the receptacle,
- wherein the tamper element is affixed to the connector via a protrusion extending from the tamper element to the connector, and
- wherein the protrusion is disposed distally of the retention member.

25. The assembly of claim 24, wherein the entire protrusion is disposed distally of the retention member.

* * * * *

EX PARTE REEXAMINATION CERTIFICATE (12216th)

United States Patent
Steele et al.

(10) Number: US 11,103,654 C1
(45) Certificate Issued: Jan. 27, 2023

(54) TAMPER-EVIDENT CLOSURE

(71) Applicant: NORDSON CORPORATION, Westlake, OH (US)

(72) Inventors: Kyle R. Steele, Windsor, CO (US); Peter D. Lewis, Loveland, CO (US); Douglas Kimmel, Nunn, CO (US)

(73) Assignee: NORDSON CORPORATION, Westlake, OH (US)

Reexamination Request:
No. 90/015,028, May 10, 2022

Reexamination Certificate for:
Patent No.: 11,103,654
Issued: Aug. 31, 2021
Appl. No.: 15/892,181
Filed: Feb. 8, 2018

(51) Int. Cl.
*A61M 5/50* (2006.01)
*A61M 5/32* (2006.01)
*A61J 1/14* (2023.01)
*B65D 41/34* (2006.01)
*A61M 5/31* (2006.01)

(52) U.S. Cl.
CPC ......... *A61M 5/5086* (2013.01); *A61M 5/3134* (2013.01); *A61M 5/3202* (2013.01); *B65D 41/3428* (2013.01)

(58) Field of Classification Search
None
See application file for complete search history.

(56) References Cited

To view the complete listing of prior art documents cited during the proceeding for Reexamination Control Number 90/015,028, please refer to the USPTO's Patent Electronic System.

*Primary Examiner* — Beverly M Flanagan

(57) ABSTRACT

A tamper-evident closure assembly includes a connector, a tamper element removably affixed to the connector, and a cap having an interior surface defining a receptacle, where a portion of the connector is within the receptacle and the cap is configured to engage with the tamper element. The tamper element is configured to be separated from the connector upon application of a removal force and to be retained within the receptacle of the cap so that it can later be removed from the receptacle. A kit for a tamper-evident closure assembly includes a cap having an interior surface defining a receptacle, a tamper element configured to engage with the cap within the receptacle, and a housing configured to receive the cap.

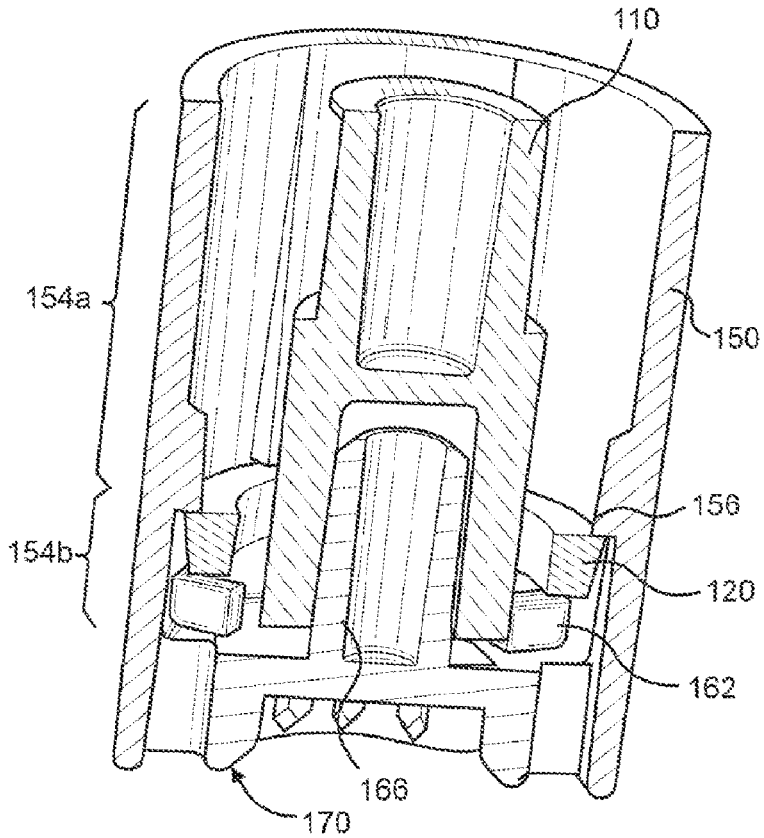

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-25 are cancelled.

\* \* \* \* \*